(12) United States Patent
Aider et al.

(10) Patent No.: US 11,628,438 B2
(45) Date of Patent: Apr. 18, 2023

(54) METHODS AND DEVICE FOR MANIPULATING OBJECTS

(71) Applicants: CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR); UNIVERSITÉ PARIS CITÉ, Paris (FR); SORBONNE UNIVERSITE, Paris (FR)

(72) Inventors: Jean-Luc Aider, Vanves (FR); Mauricio Hoyos, Creteil (FR); Gabriel Dumy, Arcueil (FR)

(73) Assignees: CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR); UNIVERSITÉ PARIS CITÉ, Paris (FR); SORBONNE UNIVERSITE, Paris (FR)

( * ) Notice: Subject to any disclaimer, the term of this patent is extended or adjusted under 35 U.S.C. 154(b) by 454 days.

(21) Appl. No.: 16/625,993

(22) PCT Filed: Jun. 29, 2018

(86) PCT No.: PCT/EP2018/067585
§ 371 (c)(1),
(2) Date: Dec. 23, 2019

(87) PCT Pub. No.: WO2019/002551
PCT Pub. Date: Jan. 3, 2019

(65) Prior Publication Data
US 2021/0154661 A1    May 27, 2021

(30) Foreign Application Priority Data

Jun. 30, 2017   (EP) .................................. 17305848

(51) Int. Cl.
*B01L 3/00*     (2006.01)
*G01N 1/40*     (2006.01)
(Continued)

(52) U.S. Cl.
CPC ........ *B01L 3/50273* (2013.01); *G01N 1/4077* (2013.01); *G01N 15/0255* (2013.01);
(Continued)

(58) Field of Classification Search
CPC ......... B01L 3/50273; B01L 2200/0636; B01L 2200/0652; B01L 2300/0816;
(Continued)

(56) References Cited

U.S. PATENT DOCUMENTS

2006/0096353 A1   5/2006   Hawkes et al.
2008/0067128 A1   3/2008   Hoyos et al.
(Continued)

FOREIGN PATENT DOCUMENTS

WO      2008122051        10/2008
WO      2017006093         1/2017
WO   WO-2017006093 A1 *   1/2017

OTHER PUBLICATIONS

European Search Report from corresponding European Patent Application No. 17305848, dated Nov. 9, 2017.
(Continued)

*Primary Examiner* — Jennifer Wecker
*Assistant Examiner* — Oyeleye Alexander Alabi
(74) *Attorney, Agent, or Firm* — Greer, Burns & Crain, Ltd

(57) ABSTRACT

A method is provided for manipulating objects in a cavity including a liquid, the method including providing in at least
(Continued)

one region of the cavity objects capable of absorbing light in a given wavelength range, forming an aggregate of the objects by submitting them to an acoustic field, and disrupting the aggregate by submitting the aggregate to a light beam emitting at the given wavelength range. Also provided is a device for manipulating objects.

15 Claims, 9 Drawing Sheets

(51) Int. Cl.
  *G01N 15/02* (2006.01)
  *G01N 15/14* (2006.01)
  *G01N 33/53* (2006.01)
  *G01N 15/00* (2006.01)

(52) U.S. Cl.
  CPC ..... *G01N 15/1429* (2013.01); *G01N 33/5302* (2013.01); *B01L 2200/0636* (2013.01); *B01L 2200/0652* (2013.01); *B01L 2300/0816* (2013.01); *B01L 2300/0864* (2013.01); *B01L 2400/0436* (2013.01); *G01N 2015/0053* (2013.01)

(58) Field of Classification Search
  CPC ..... B01L 2300/0864; B01L 2400/0436; B01L 2400/0439; B01L 3/502761; G01N 1/4077; G01N 15/0255; G01N 15/1429; G01N 33/5302; G01N 2015/0053; G01N 21/6458; G01N 21/6486; G01N 2001/4094; G01N 2021/1729
  See application file for complete search history.

(56) References Cited

U.S. PATENT DOCUMENTS

| | | |
|---|---|---|
| 2009/0029870 A1* | 1/2009 | Ward ................... G01N 27/447 210/695 |
| 2009/0158823 A1 | 6/2009 | Kaduchak et al. |
| 2012/0225475 A1 | 9/2012 | Wagner et al. |
| 2013/0327130 A1 | 12/2013 | Hoyos et al. |
| 2015/0037863 A1 | 2/2015 | Bazou et al. |
| 2015/0285719 A1 | 10/2015 | Hoyos et al. |
| 2016/0231223 A1 | 8/2016 | Wang et al. |
| 2016/0282264 A1* | 9/2016 | Wagner ............. G01N 15/1484 |
| 2018/0104693 A1* | 4/2018 | Merten ............. B01L 3/502784 |

OTHER PUBLICATIONS

International Search Report from corresponding International Patent Application No. PCT/EP2018/067585, dated Aug. 1, 2018.

* cited by examiner

METHODS AND DEVICE FOR MANIPULATING OBJECTS

BACKGROUND

The present invention pertains to the field of manipulation of objects in a cavity comprising a liquid. In particular, the invention relates to methods and devices for manipulating, separating, recovering and imaging such objects using an acoustic field and an electromagnetic field.

BACKGROUND OF INVENTION

In conventional manner, objects in a liquid may be handled and sorted by means of various technologies: membranes, filters, centrifugation, magnetic fields, electric fields or acoustic fields.

Acoustic manipulation of objects has been intensively studied in the recent years. For instance, US 2006/0096353A1 discloses an apparatus using acoustic manipulation for directing objects in a liquid, US 2015/0037863 discloses a method for forming multilayer aggregate of layers using acoustic forces, especially for forming 2D and 3D cells aggregates or US 2015/0285719 discloses a method of forming an aggregate using a modulated pulsed acoustic field.

Acoustic manipulation is based on acoustic radiation force which creates aggregates of objects in levitation. It occurs in a cavity, referred to as an acoustic resonator, comprising an emitting wall and a reflective wall, when an acoustic standing wave verifying the condition $\lambda=2\times h$ is applied (h being the height between the emitting wall and the reflective wall). Objects are then submitted to an acoustic radiation force $F_{ac}$ which may be defined as $$\vec{F}_{ac} = \frac{\pi}{4} \langle E_{ac} \rangle k d_p^3 F_y \sin(2kz)\vec{e}_z \quad (1)$$

wherein $\langle \cdot \rangle$ denotes time averaging, $d_p$ is the particle diameter, $\langle E_{ac} \rangle$ is the acoustic energy density inside the cavity averaged over one period of the acoustic wave, $$k = \frac{2\pi}{\lambda}$$

is the wave number of the acoustic plane, $F_y$ is the acoustic contrast factor and z is the axial position of particle between the emitting wall and the reflective wall.

Said acoustic radiation force pushes objects in levitation towards the nodes or the antinodes of the acoustic waves at different speed depending on their acoustic contrast factor and diameter. The acoustic radiation force also comprises a transverse component responsible for the aggregation of objects once in the levitation plane. The acoustic contrast factor can be written as follows:

$$F_Y = \frac{1 + \frac{2}{3}\left(1 - \frac{\rho_f}{\rho_p}\right)}{2 + \frac{\rho_f}{\rho_p}} - \frac{\rho_f c_f^2}{3\rho_p c_p^2} \quad (2)$$

wherein $\rho_p$ is the density of the objects in a medium of density $\rho_f$, $c_p$ is the celerity of sound in the objects and $c_f$ is the celerity of sound in the liquid.

In view of the above, objects exhibiting the same acoustic contrast factor and the same size will behave in the same manner within the liquid and cannot be effectively sorted. There is therefore a need for a contactless technology capable of manipulating or sorting objects, especially objects with the same or similar acoustic contrast factor.

Moreover, the use of an acoustic field for sorting objects dictates the design of the associated device. Acoustic resonator, such as disclosed in US 2008/0067128 A1, comprises at least three sheets received within a plate including at least two portions. Such complex design is required to manufacture a device with at least two outlets at different heights. Acoustic sorting of the prior art is indeed based on the separation of objects at different level along the axis parallel to the wave propagation direction.

Thus, another objective underlying the present invention is to provide an easy to manufacture and easy to handle device implementing high throughput acoustic sorting.

SUMMARY

The needs of the invention are achieved by the methods and device as claimed. Especially, the method of present invention uses a light beam to expulse objects (also referred to as particles) from an aggregate formed by an acoustic field. The objects are expulsed within the plane of levitation, therefore enabling easy sorting of the objects with outlets positioned at the same height along the axis parallel to the direction of propagation of the acoustic wave. The methods described within the present invention may be referred to as photoacoustophoresis methods.

In a first aspect, the present invention relates to a method for manipulating objects in a cavity comprising a liquid, said method comprising:

a) providing in at least one region of the cavity objects capable of absorbing light in a given wavelength range;
b) forming an aggregate of the objects by submitting them to an acoustic field; and
c) disrupting the aggregate by submitting said aggregate to a light beam emitting at the given wavelength range.

According to one embodiment, the power of the light beam is ranging from 10 μW to 200 mW. According to one embodiment, the amplitude of the acoustic field is ranging from 0.1 V to 50 V. According to one embodiment, the volume fraction of the objects within the liquid is ranging from 0.025% to 65%. According to one embodiment, the acoustic field is a pulsed acoustic field. According to one embodiment, the frequency of the acoustic field is in the range from $0.5f_0$ to $1.5f_0$, wherein $f_0$ is a resonance frequency of the cavity. According to one embodiment, the objects are fluorescents.

In a second aspect, the present invention relates to a method for separating objects in a cavity comprising a liquid, said method comprising:

a) providing in at least one region of the cavity objects comprising a first plurality of objects capable of absorbing light in a first wavelength range and a second plurality of objects not capable of absorbing light in the first wavelength range;
b) forming an aggregate of the first plurality of objects and the second plurality of objects by submitting them to an acoustic field; and c) expulsing the first plurality of objects from the aggregate by submitting the aggregate to a light beam emitting at the first wavelength range.

According to one embodiment, the method for separating objects further comprises the steps of:

d) flowing the liquid within the cavity; and
e) recovering the expulsed objects in a first outlet.

According to one embodiment, the second plurality of objects absorbs light in a second wavelength range not overlapping with the first wavelength range. According to one embodiment, the method for separating objects further comprises the step of submitting the aggregate to a light beam emitting at the second wavelength range. According to one embodiment, the first plurality of objects has substantially a same acoustic contrast factor than the second plurality of objects.

In a third aspect, the present invention relates to a method for acquiring at least one image of objects in a cavity comprising a liquid, said method comprising:

a) manipulating or separating the objects by using the method according to the invention;
b) illuminating the at least one region of the cavity; and
c) acquiring at least one image of said illuminated objects.

In a fourth aspect, the present invention relates to a device for separating objects in a liquid, said device comprising:

at least one cavity extending along a longitudinal axis, having a cross-section that present a width measured along a first transverse axis and a height measured along a second transverse axis perpendicular to the first transverse axis; the cavity having first and second walls along the second transverse axis, at least a first inlet in liquid communication with the cavity and at least first, second and third outlets in liquid communication with the cavity, wherein the first outlet is arranged on the first transverse axis between the second and third outlets;
at least one acoustic wave generator which generates acoustic field in a first region of the cavity from one of the walls; and
at least one light source which emits light beam in the first region of the cavity.

According to one embodiment, the device further comprises second and third inlets wherein the first inlet is arranged on the first transverse axis between the second and third inlets.

Definitions

In the present invention, the following terms have the following meanings:

"About" preceding a figure means plus or minus 10% of the value of the figure, preferably plus or minus 5%, more preferably plus or minus 1%.

"Absorbing" refers to the absorption of electromagnetic radiation, especially light.

"Aggregate of objects" refers to a layer of objects satisfying all of the following features: at least two objects comprised in said layer, in particular at least 10%, better 25%, preferably 50% of the objects comprised in said layer, are in contact, and said layer presents, on at least a portion of its length, a succession of objects when displacing along at least one of its transverse dimensions.

"Amplitude" as used herein refers to the peak to peak amplitude. The amplitude of the acoustic wave is proportional to the voltage applied to the acoustic wave generator.

"Aqueous solution" is defined as a unique-phase solution wherein water is the main chemical species in terms of molar ratio and/or in terms of mass and/or in terms of volume in respect to the other chemical species contained in said aqueous solution.

"Cavity" refers to a pathway, a channel or conduit, closed or preferably with at least one inlet and at least one outlet, having an interior shape selected from rectangular (also referred to as channel), square, circular, or polygonal with preferably from 3 to 10 edges.

"Light" refers to an electromagnetic radiation, preferably an electromagnetic radiation having wavelengths in a range from 10 nm to 10 000 nm (i.e. from infrared to ultraviolet light), more preferably electromagnetic radiation having wavelengths in a range from about 400 to about 800 nm (i.e. visible light).

"Longitudinal axis" refers to the line joining the centers of gravity of the cross-sections of the cavity. The longitudinal axis may be straight or curved.

"Objects": refers to a particle and encompasses biological cells, such as, eukaryotic and prokaryotic cells, archaea, bacteria, mold, plant cells, microalgae, yeast, protozoa, ameba, protists, animal cells; cell organelles; organic/inorganic elements or molecules; microspheres; and droplets of immiscible liquid such as oil in water.

"Volume fraction of the object": refers to ratio between the volume of the objects divided by the volume of all different objects of the mixture comprising the object and the liquid.

(e)-(f) as soon as the green light excitation is turned off, the aggregation process starts again and the aggregate goes back to its original shape.

Figure 11:
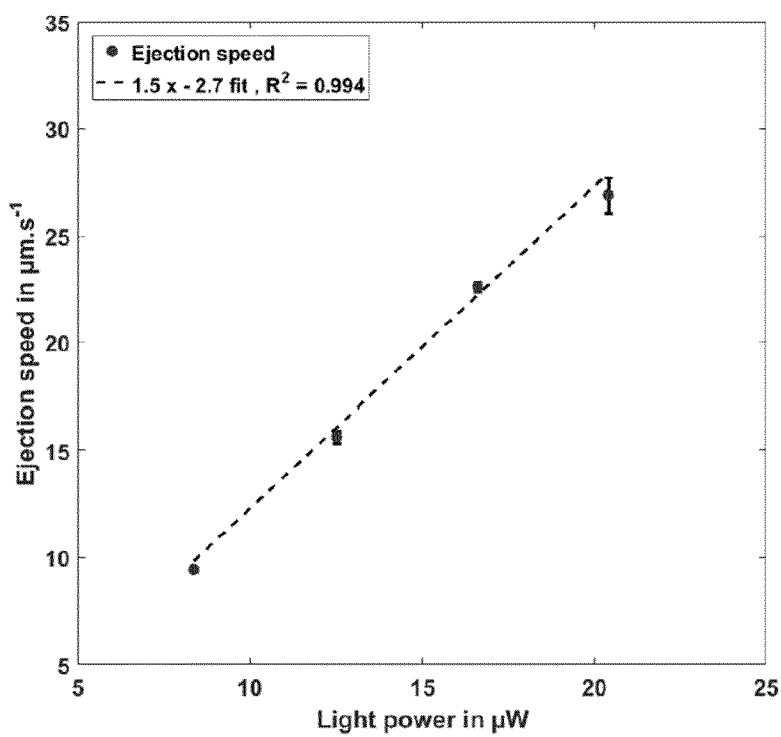

FIG. 11 illustrates the ejection velocity of the objects from the aggregate as a function of the illumination power.

Figure 12:
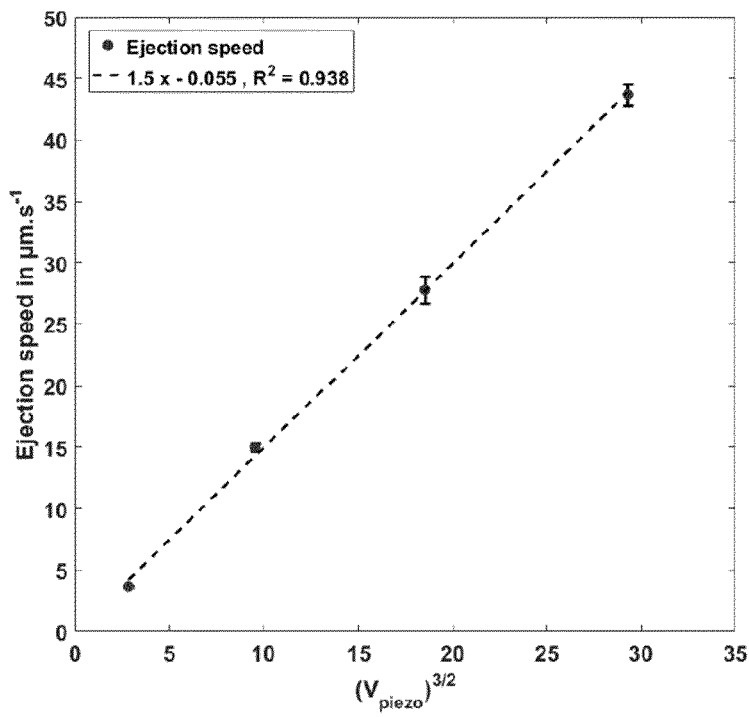

FIG. 12 illustrates the ejection velocity of the objects as a function of the amplitude of the acoustic field.

Figure 13:
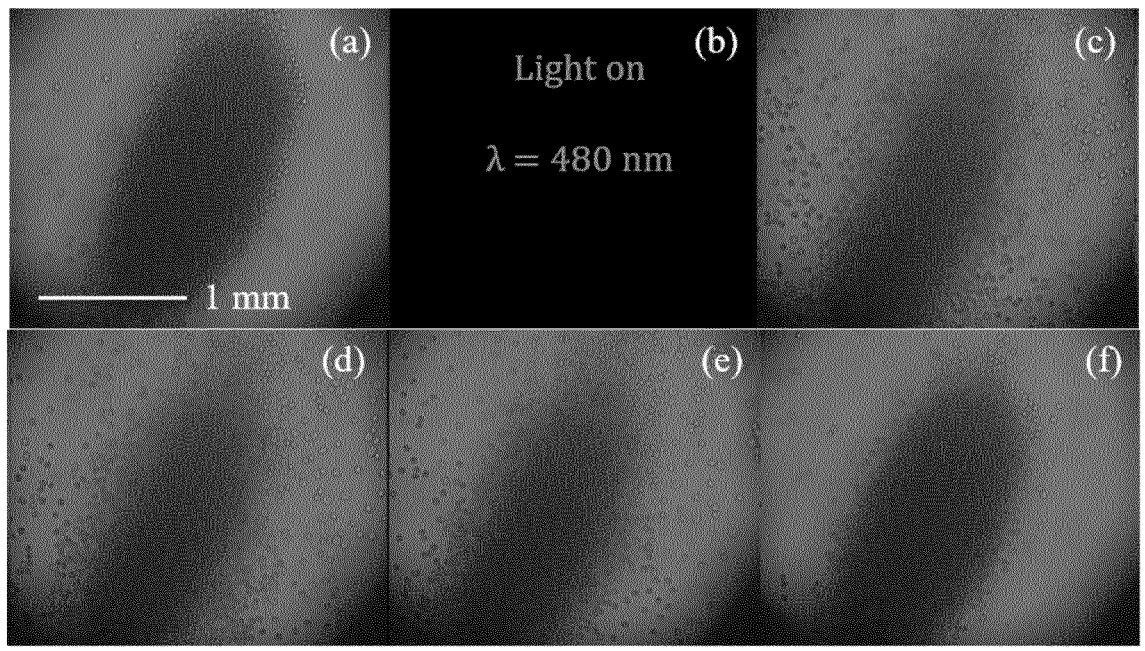

FIG. 13 illustrates an aggregate of red blood cells:
  (a) submitted to blue illumination ($\lambda_{light}$=488 nm);
  (b) under the photoacoustic interaction;
  (c)-(d) the aggregate explodes;
  (e)-(f) as soon as the blue light excitation is turned off, the aggregation process starts again and the aggregate goes back to its original shape.

Figure 14:
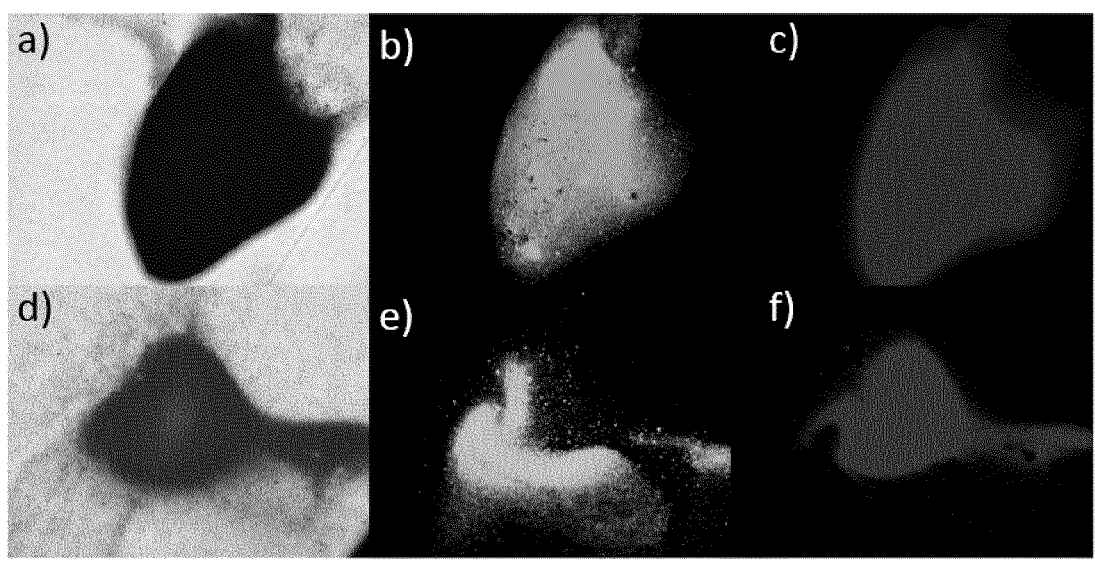

FIG. 14 illustrates separation of a binary mixture of 1.62 µm red fluorescent objects and 0.883 µm green fluorescent objects.

Figure 15:
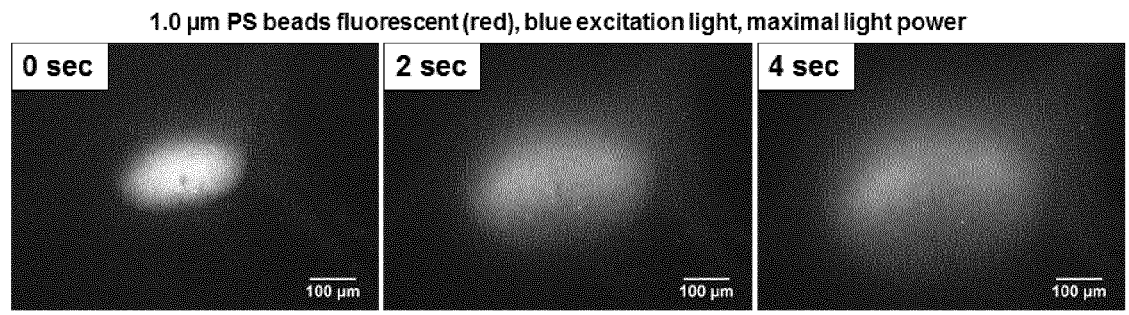

FIGS. 15a, 15b and 15c illustrate an explosion of 1.0 µm fluorescent polystyrene particles.

Figure 16:
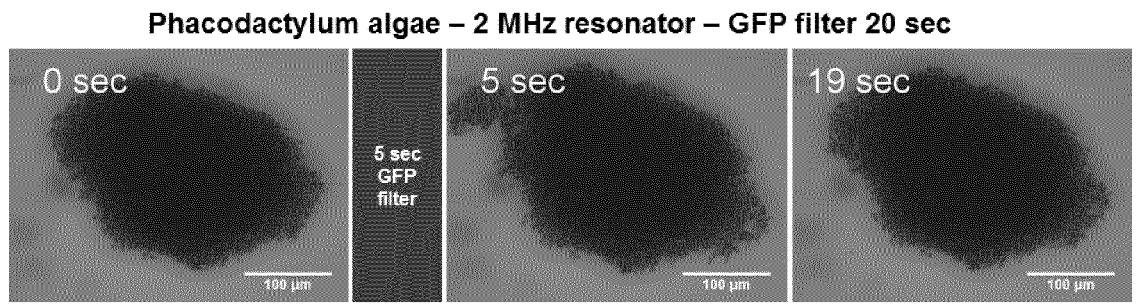

FIG. 16 illustrates the influence of the blue light on the levitating aggregate of algae (phacodactylum)

Figure 17:
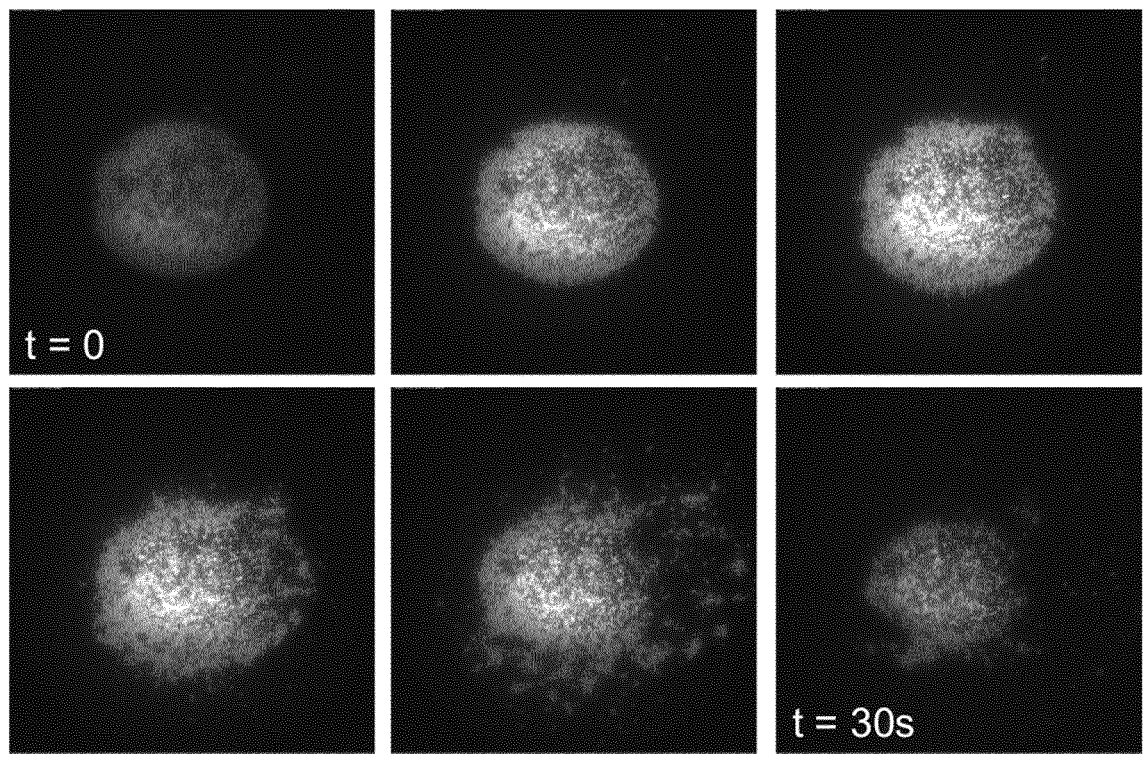

FIG. 17 illustrates creation of nano-rods aggregate and dispersion under illumination.

Figure 18:
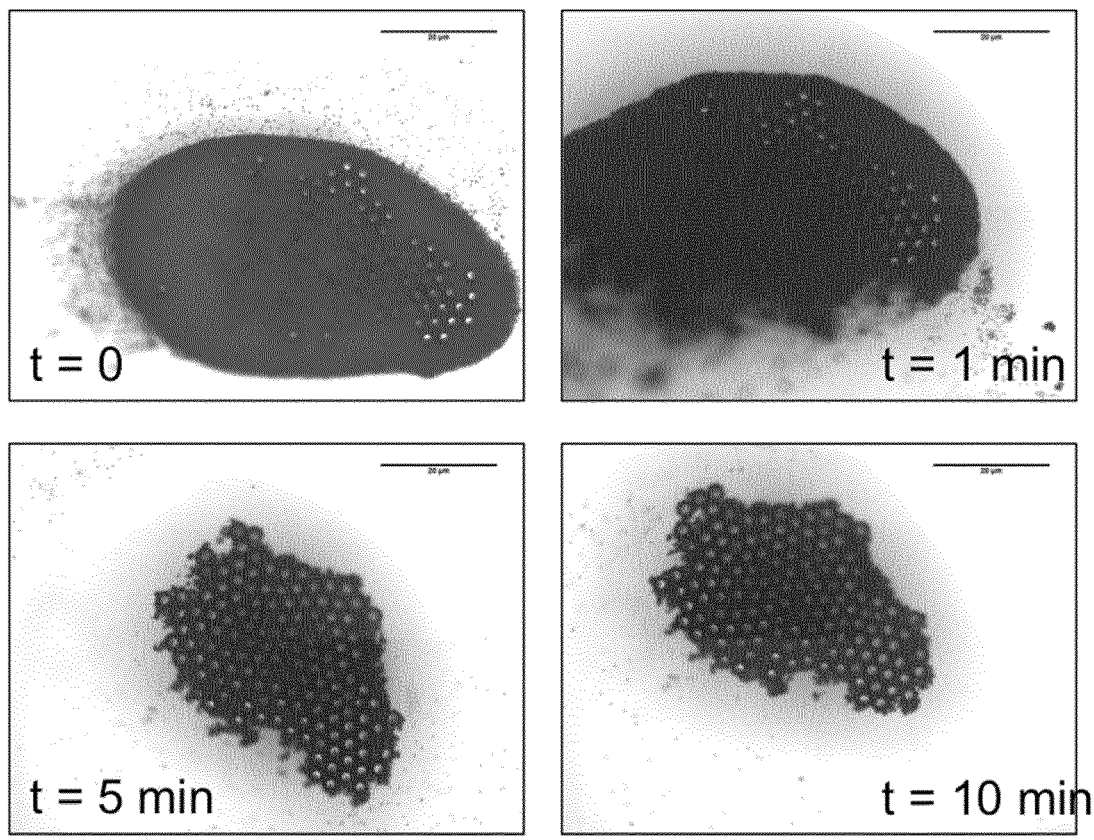

FIG. 18 illustrate an example of isolation of large light-insensitive particles surrounded by a large number of particles that absorb light.

DETAILED DESCRIPTION

The following detailed description will be better understood when read in conjunction with the drawings. For the purpose of illustrating, the devices are shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

According to a first aspect, this invention relates to a method for manipulating objects in a cavity comprising a liquid. The method according to invention comprises the following steps:
  providing in at least one region of the cavity objects capable of absorbing light in a given wavelength range;
  forming an aggregate of the objects by submitting them to an acoustic field; and
  disrupting the aggregate by submitting said aggregate to a light beam emitting at the given wavelength range.

The aggregate is submitted to a light beam while simultaneously under an acoustic field.

Figure 1:
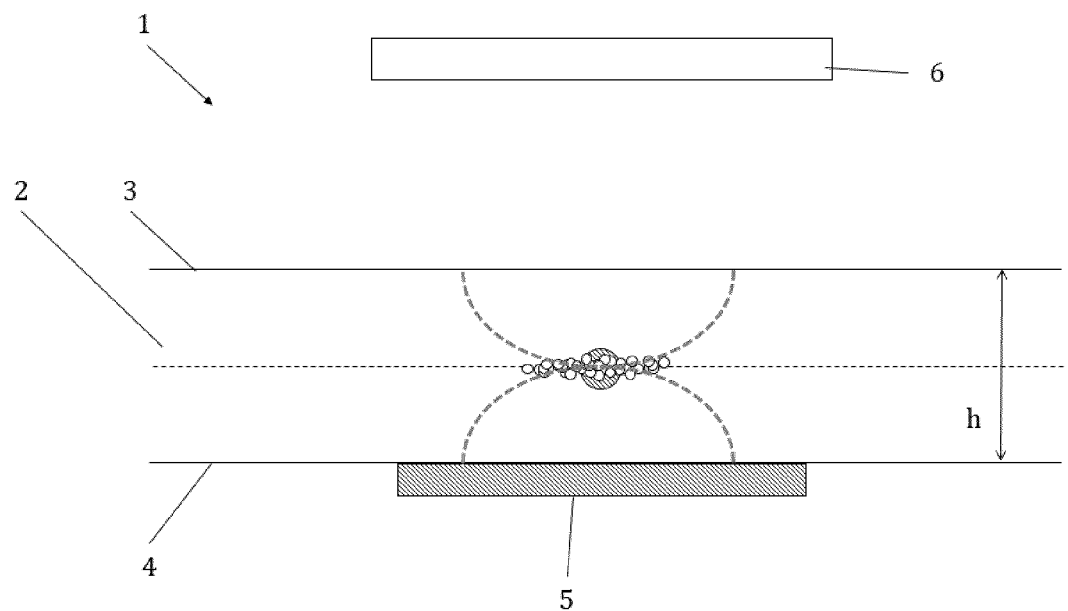
FIG. 1 shows a sectional view of one embodiment of a device for carrying out of a method according to the invention wherein the objects comprise two pluralities of objects prior to illumination of the objects with a light beam.
Figure 3:
FIG. 3A shows a partial top view of the device according to FIG. 1.
FIG. 3B shows a partial top view of the device according to FIG. 2.

The method of the present invention allows first to form a layer of objects, also called, aggregate using acoustic field to perform acoustic focusing. As depicted in FIG. 1 and FIG. 3A, in the presence of only an acoustic field 8 generated by an acoustic field generator 5, the objects form an aggregate at mid height of the cavity 2 between the emitting wall 4 and the reflective wall 3.

At least one extremum of the acoustic pressure is formed within the liquid by the acoustic field. The layer of objects is preferably focused at an extremum of acoustic pressure (an acoustic node or antinode called a levitation plane) formed within the liquid by the generated acoustic waves. For example, a plurality of layers of distinct objects is formed, each of these layers being present at a distinct acoustic pressure extremum.

The layer of objects that is formed may have a shape which is elongated and may be, for example, oval or rectangular in shape when viewed in a direction perpendicular to the plane of flattening of the layer. In a variant, the layer of objects that is formed may have a circular or square shape when viewed in a direction perpendicular to its plane of flattening.

The objects of the aggregate are then irradiated by the light beam, migrate along the levitation plane and are gradually expulsed from the aggregate itself.

Figure 2:
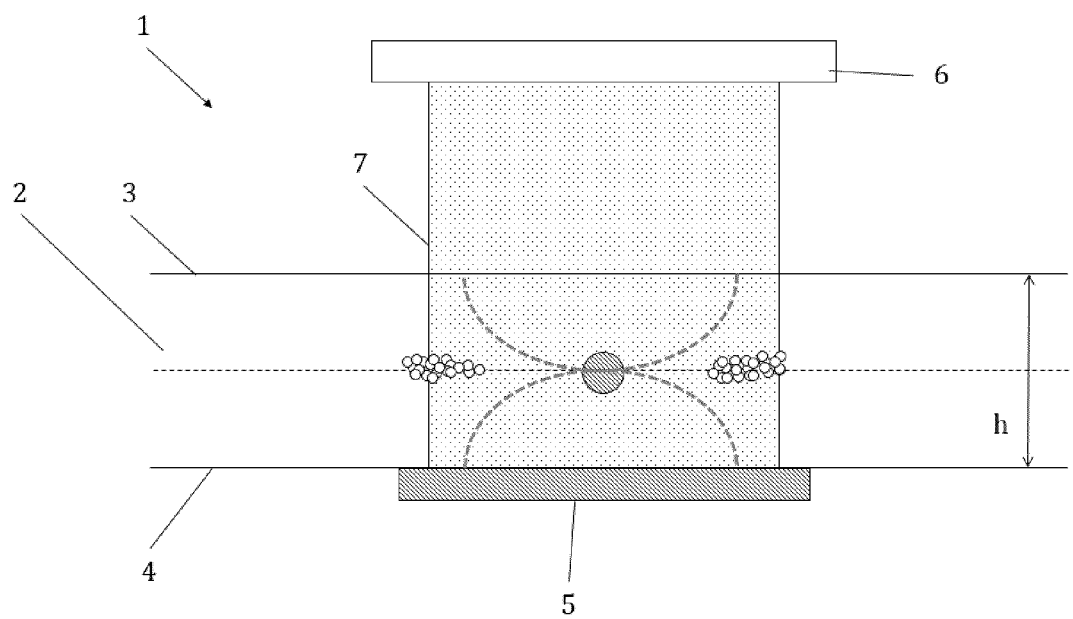
FIG. 2 shows a sectional view of one embodiment of a device for carrying out of a method according to the invention wherein the objects comprise two pluralities of objects during illumination of the objects with a light beam.

As illustrated in FIG. 2 and FIG. 3B, when simultaneously submitted to an acoustic filed 8 and a light beam 7 emitted by a light source 6, the objects absorbing the wavelength emitted by the light source (here the white beads) are ejected from the aggregate while the objects non-absorbing (here the crosshatch bead) remain unchanged.

The expulsion of the objects may be observed only if these objects are illuminated with a light beam at the wavelength corresponding to the objects absorption wavelength band. The objects escape the aggregate while remaining in levitation. According to the Applicant, this is due to the fact that the primary radiation force is not affected but the transversal force is balanced.

The present invention may advantageously allow separating and collecting the objects continuously without damage within the levitation plane. The device used in the method according to the invention may comprise a standard ultrasound and illumination equipment.

In another of its aspects, the invention relates to a method for separating objects in a cavity comprising a liquid. Said method comprises the steps of:
  providing in at least one region of the cavity objects comprising a first plurality of objects capable of absorbing light in a first wavelength range and a second plurality of objects not capable of absorbing light in the first wavelength range;
  forming an aggregate of the first plurality of objects and the second plurality of objects by submitting them to an acoustic field; and
  expulsing the first plurality of objects from the aggregate by submitting the aggregate to a light beam emitting at the first wavelength range.

The said method allows the separation of objects having substantially the same acoustic contrast factor. The method according to the present invention further allows the sorting of rare objects among a population of abundant objects; especially large rare objects among a population of small abundant objects. Indeed, due to their sizes, the large rare objects will be quickly focused in the levitation plane and then cannot be effectively sorted among the abundant objects by mere acoustophoresis.

The objects concentrated and then expelled by the method according to the invention may be selectively guided toward a first outlet of the cavity.

Consequently, in on embodiment, the method further comprises the steps of:
  flowing the liquid within the cavity; and
  recovering the expulsed objects in a first outlet.

Figure 4:
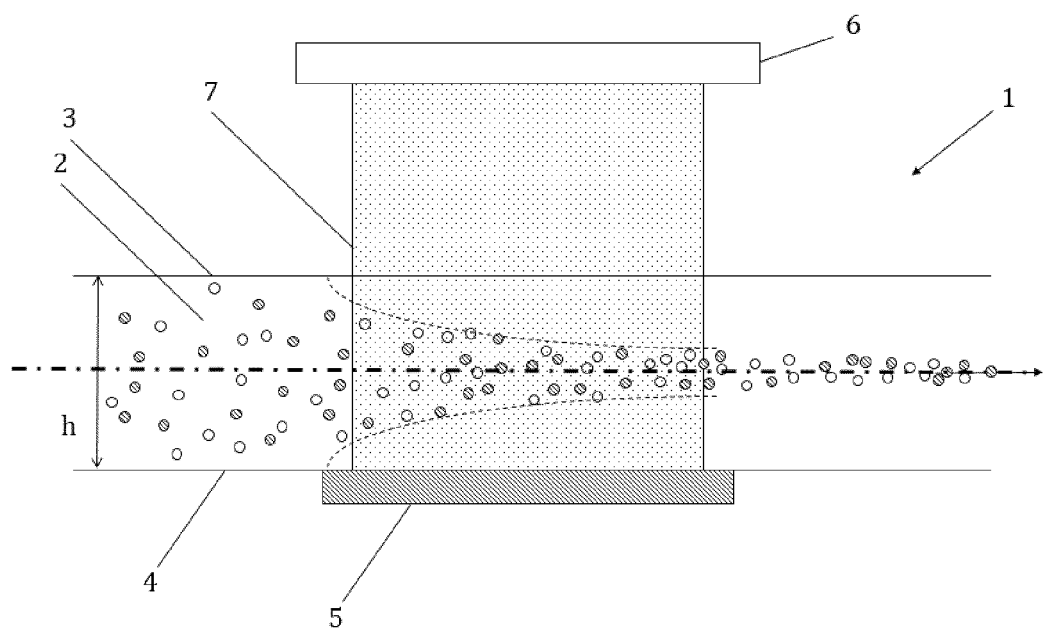
FIG. 4 shows a sectional view of one embodiment of a device for carrying out of a method according to the invention wherein the objects comprise two pluralities of objects.
Figure 5:
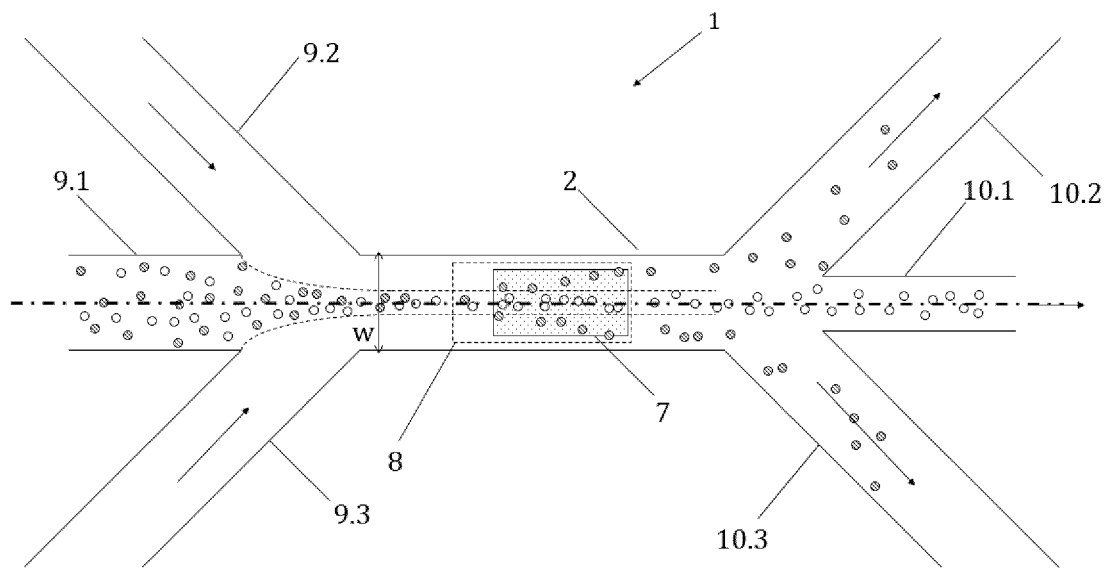
FIG. 5 shows a top view of the device according to FIG. 4.

The method according to the invention is illustrated in FIG. 4 and FIG. 5. FIG. 4 shows a device for manipulating and separating objects 1 comprising a first wall 3 and a second wall delimiting the height of a cavity 2. The first wall 3 is a reflective wall and the second wall is a transmitter wall 4 to which is fastened and acoustic wave generator 5 for generation of an acoustic field 8. FIG. 4 further depicts a light source 6 illuminating an illumination area 7 within the cavity 2. Said cavity 2 comprises a liquid and objects comprising a first plurality of objects absorbing in the wavelength of the light source (crosshatched beads) and a second plurality of not absorbing objects (white beads). As illustrated in FIG. 4, when submitted to an acoustic field 8, the objects form an aggregate in a levitation plane at mid height of the cavity 2. While simultaneously under a light beam 7 and an acoustic field 8 in a first region of the cavity 2, the absorbing objects are ejected from the aggregate (see FIG. 5). In a state of flow, the objects may be sorted by positioning a first central outlet 10.1 for non-absorbing objects and second and third outlets (10.2, 10.3) for absorbing objects ejected from the aggregate. In order to improve sorting, the device may comprise more than one inlet 9.1. By using second and third inlets 9.2, 9.3, supplied with a buffer solution, on each side of the first inlet 9.1, supplied with the liquid comprising objects, hydrodynamic focusing centers the objects within the width w of the cavity.

According to one embodiment, the second plurality of objects does not absorb light. According to one alternative embodiment, the second plurality of objects absorbs light in a second wavelength range not overlapping with the first wavelength range.

In the latter embodiment, the method of separating objects may further comprise the step of submitting the aggregate to a light beam emitting at the second wavelength range.

In one embodiment, the method comprises the steps of:
providing in at least one region of the cavity objects comprising a first plurality of objects capable of absorbing light in a first given wavelength range, a second plurality of objects capable of absorbing light in a second given wavelength range and a third plurality of objects;
forming an aggregate of the first plurality of objects, the second plurality of objects and the third plurality of objects by submitting them to an acoustic field;
expulsing the first plurality of objects from the aggregate by submitting the aggregate to a light beam emitting at the first given wavelength range; and
expulsing the first plurality of objects from the aggregate by submitting the aggregate to a light beam emitting at the second given wavelength range.

According to one embodiment, the third plurality of objects does not absorb light. According to one alternative embodiment, the third plurality of objects absorbs light in a third wavelength range not overlapping with the first and the second wavelength ranges.

In view of the foregoing, it is apparent to one skilled in the art that the method may be implemented as follows:
providing in at least one region of the cavity objects comprising n pluralities of objects, each plurality of objects being capable of absorbing light in a wavelength range and none of the n wavelength ranges being overlapping;
forming an aggregate of the objects by submitting them to an acoustic field; and
for i=1 . . . n, expulsing the $i^{th}$ plurality of objects from the aggregate by submitting the aggregate to a light beam emitting at the $i^{th}$ wavelength range.

Figure 6:
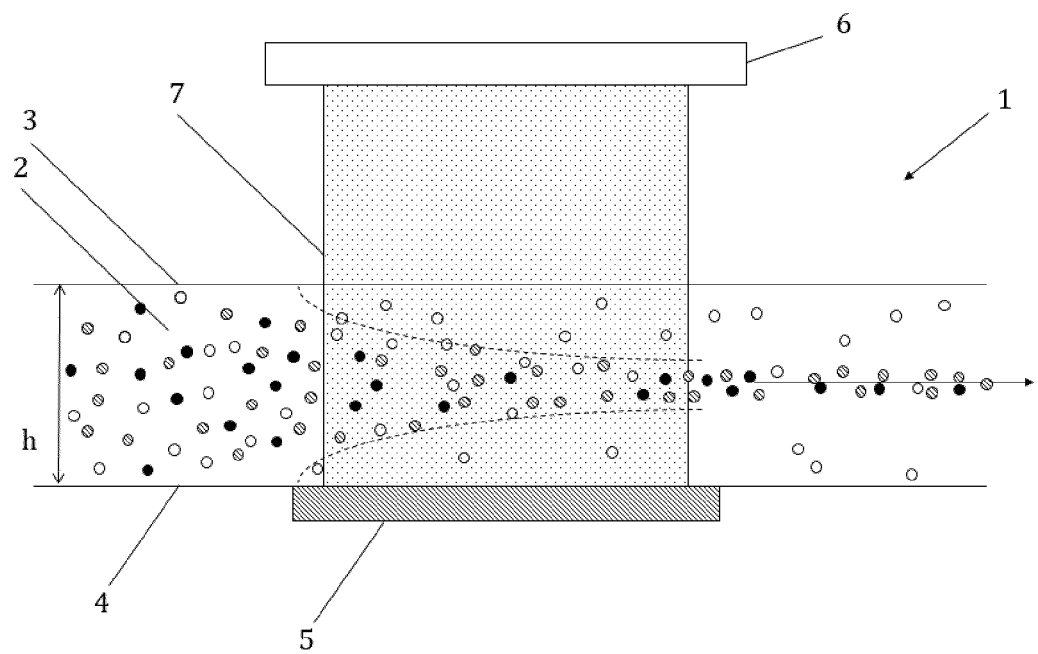
FIG. 6 shows a sectional view of one embodiment of a device for carrying out of a method according to the invention wherein the objects comprise three pluralities of objects.
Figure 7:
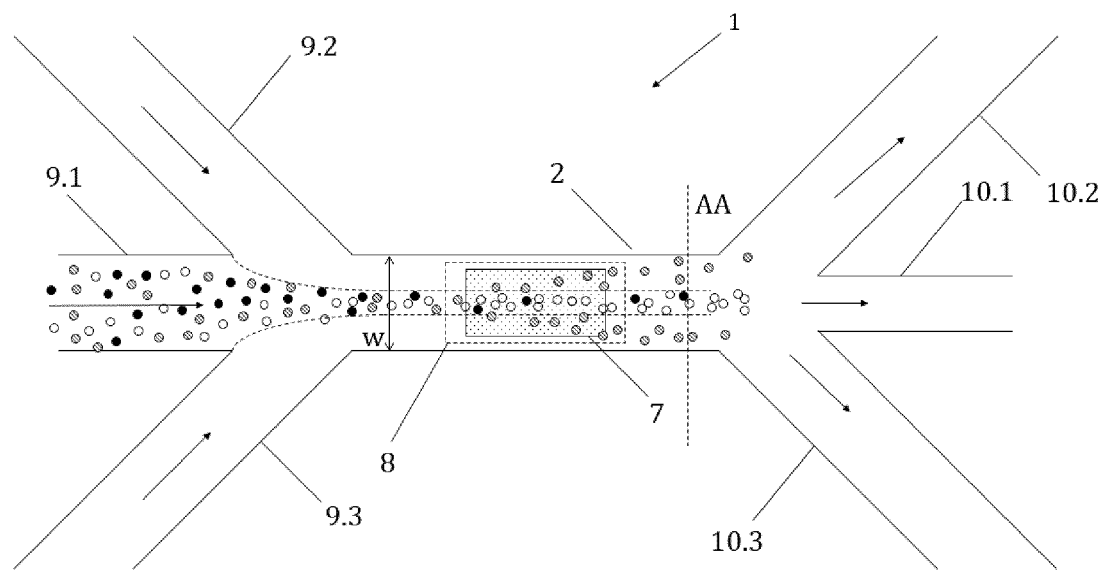
FIG. 7 shows a top view of the device of FIG. 6.

As illustrated in FIG. 6 and FIG. 7, the method may be carried out with more than one plurality of objects and even more than two pluralities of objects. FIG. 6 shows indeed three pluralities of objects: optically and acoustically active objects (crosshatched beads), acoustically active objects (black beads) and non-active objects (white beads). The acoustically active objects are focused in the levitation plane by acoustic migration while the non-active objects do not migrate. Once under a light beam 7, the optically active objects are ejected from the aggregate and migrate.

Figure 8:
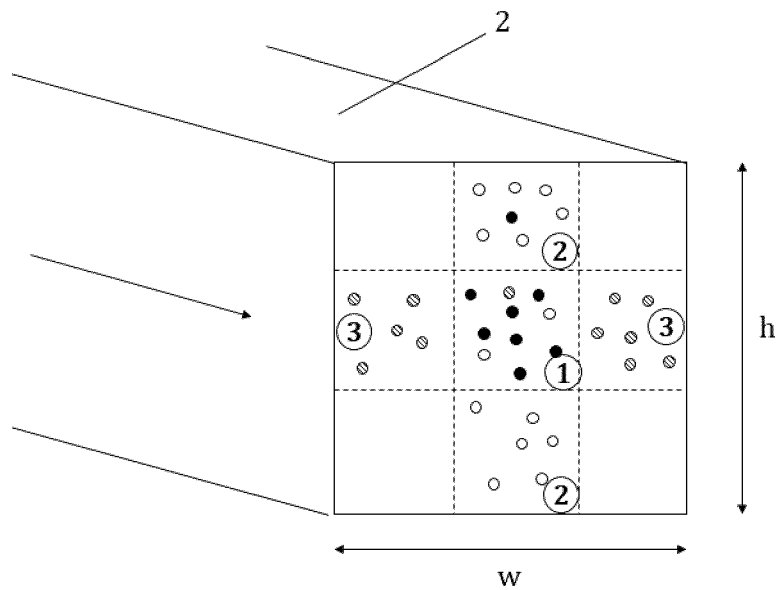
FIG. 8 is a view according to AA of the cavity used in FIG. 7.

Consequently, the method of the present invention may be used for sorting three pluralities of objects or more. As depicted in FIG. 8, the acoustically active species may be collected in the center of the levitation plane (1), while the non-active species may be collected in the center of the cavity along the width w (2), perpendicular to the acoustic wave direction and the acoustically and optically species may be collected on the sides of the levitation plane in the center of the cavity along the height h (3).

In another embodiment, not represented, each plurality of objects is optically active but with non-overlapping absorption spectrum; thus enabling sequential sorting.

The invention may, in an exemplary embodiment, relate to a method for acquiring at least one image of objects in a cavity comprising a liquid. Said method comprising:
manipulating or separating the objects by using a method as described above;
illuminating the at least one region of the cavity by means of an illumination system; and
acquiring at least one image of said illuminated objects by means of an acquisition system.

According to one embodiment, the steps of illuminating and acquiring at least one image are performed simultaneously to the manipulating or separating step. According to one embodiment, the steps of illuminating and acquiring at least one image are performed subsequently to the manipulating or separating step.

According to one embodiment, the illumination system used for imaging the objects is also used for submitting the objects to the light beam used in the manipulating or sorting methods.

Independently, or in combination with the foregoing, the present invention, in another of its aspects, relates to a device for separating objects in a liquid.

As depicted in FIG. 6 and FIG. 7, said device comprises:
at least one cavity 2 extending along a longitudinal axis, having a cross-section that presents a width (w) measured along a first transverse axis and a height (h) measured along a second transverse axis perpendicular to the first transverse axis; the cavity 2 having first and second walls 3, 4 along the second transverse axis, at least a first inlet 9.1 in liquid communication with the cavity 2 and at least first, second and third outlets 10.1, 10.2, 10.3 in liquid communication with the cavity 2, wherein the first outlet 10.1 is arranged on the first transverse axis between the second and third outlets 10.2, 10.3;
at least one acoustic wave generator 5 which generates acoustic field 8 in a first region of the cavity from one of the walls; and at least one light 6 source which emits light beam 7 in the first region of the cavity.

Within the present invention, the first region is defined as the region wherein the cavity is submitted to both the acoustic field and the light beam. As it is apparent to one skilled in the art, the acoustic wave generator may generate an acoustic field within a second region encompassing the first region and the light source may generate a light beam on a third region encompassing the first region. The first region being in that case the intersection of the second and third regions.

In one embodiment, the at least first, second and third outlets 10.1, 10.2, 10.3 are arranged on the same height on the second transverse axis. In one embodiment, the device further comprises second and third inlets 9.2, 9.3, wherein the first inlet 9.1 is arranged on the first transverse axis between the second and third inlets 9.2, 9.3. The latter embodiment allows hydrodynamic focusing of the objects at the center of the cavity 2.

The method described above may be used in at least one of the following applications: methods of sorting species, for example rigid or deformable objects, polydisperse objects, biological cells, notably blood cells, for example cancer cells present in a specimen of blood or globules, bacteria, colloidal or non-colloidal emulsions, proteins or liposomes; methods of diagnosis or analysis; methods of purification, enrichment or depletion of species; methods of synthesis of species; methods of modification of physical or chemical characteristics of species; methods of medicinal product research; methods of mixing or methods of measuring diffusion coefficients.

The method according to the invention may, in particular, be used for the purposes of separating objects initially included in a mixture of polydisperse objects.

As depicted in FIG. 2 and FIG. 3B, the method of the invention may be used for isolating rare cells of interest (crosshatched bead) among abundant non-interesting cells (white beads). Especially, rare cells non-absorbing at chosen wavelength, such as circular tumoral cells, may be identified among abundant cells, such as red blood cells, absorbing in said chosen wavelength, even in the case of similar acoustic contrast factor of the two populations. The non-interesting absorbing objects are expelled from the illuminated area 7 while the interesting non-absorbing objects remains at its position under acoustic levitation. As apparent to one skilled in the art, the cells of interest may mutatis mutandis be absorbing at a chosen wavelength and the abundant cells may be non-absorbing at said chosen wavelength.

The absorption differences between polydisperse objects may enable the objects to be separated along the width of the cavity.

The method according to the invention may also enable filterless filtration to be carried out by selective acoustic focusing and selective light expulsion of the handled objects.

When the liquid is in a state of flow, the modification of the position of the objects may enable said objects to be guided selectively toward a given outlet of the cavity.

According to one embodiment, the liquid is an aqueous solution, an organic solution or a mixture thereof. According to one embodiment, the liquid is an emulsion. According to one embodiment, the liquid is a biological liquid such as blood, plasma or any cell culture medium.

According to one embodiment, the liquid is transparent to light, especially to visible radiation. The liquid may be at rest when the device is in operation. In an alternative embodiment, the liquid is flowing when the device is in operation.

According to one embodiment, the objects are capable of absorbing light in a given wavelength range. According to one embodiment, the objects comprises a first plurality of objects capable of absorbing light in a given wavelength range and a second plurality of objects not capable of absorbing light in a given wavelength range. The first plurality of objects may have substantially a same acoustic contrast factor than the second plurality of objects. According to one embodiment, the objects comprise n pluralities of objects, with n ranging from 1 to 10, 100 or 1 000.

According to one embodiment, the objects are fluorescent.

According to one embodiment, the objects are rigid or deformable objects, polydisperse or monodispersed objects.

According to one embodiment, the objects are selected from rigid, elastic, mineral or biological objects. According to one embodiment, the objects are selected from algae, microorganisms, bacteria, viruses, DNA, proteins or leavening. According to one embodiment, the objects are selected from colloidal objects. According to one embodiment, the objects are selected from cells, parts of cells such as cell debris, or cluster of cells; such as for instance blood cells, cancellous cells or epithelial cells. According to one embodiment, the objects are selected from phospholipids, liposomes or vesicles. According to one embodiment, the objects are selected from micro-objects such as metallic micro fibers; or nanoobjects such as carbon nanotubes or mixture thereof. According to one embodiment, the objects are self-propelled objects such as bacteria in biological or ionic liquids or micro-/nano-robots.

The objects may be, for example, monodisperse or polydisperse absorbing biological cells. In the latter case, the method according to the invention may be used, for example, in procedures for sorting said biological cells. In a variant, the objects may be monodisperse or polydisperse fluorescent biological cells marked with a fluorescent dye molecule.

The mean size of the objects present within the cavity may, for example, be less than or equal to 50 micrometers. The term "mean size" denotes the statistical object size at half the population, called D50.

According to one embodiment, the volume fraction of objects within the liquid is higher of 0.025%, notably ranging from 0.025 to 65%, preferably from 0.025 to 35%, more preferably from 5 to 20%.

The height of the cavity may, at least at a position along the longitudinal axis at which the acoustic waves are generated, be greater than or equal to ten times the mean size of the objects present within the cavity.

The cavity extends along a longitudinal axis, having a cross-section that present a width measured along a first transverse axis and a height measured along a second transverse axis perpendicular to the first transverse axis; the cavity having first and second walls along the second transverse axis.

The cavity may have a substantially constant cross section with respect to movement along its longitudinal axis. The cavity may have a rectangular cross section over at least a portion of its length, notably over the whole of its length. In a variant, the cavity may have a square or circular cross section over at least a portion of its length, notably over the whole of its length.

The cavity may have a height in the range from 20 micrometers to a few millimeters, preferably from 100 micrometers to 500 micrometers, over at least a portion of its length, notably over the whole of its length. The width of the cavity may be constant or variable with respect to movement along the longitudinal axis of the cavity. The cavity may have a width in the range from 1 mm to 30 mm, preferably from 5 mm to 20 mm, over at least a portion of its length, notably over the whole of its length.

According to one embodiment, the cavity is a cylindrical cavity. The diameter of said cylindrical may be in the range from 10 to 30 millimeters, such as for example 10, 12, 14, 16, 18, 20, 22, 24 or 26 millimeters.

At least one of the first and second walls of the cavity may be moveable in order to insert a medium inside the cavity, such as, by means of non-limiting example, a liquid medium comprising multiple objects.

At least one of the first and second walls of the cavity, may include, or notably consist of, a material chosen from among the following: mineral or organic glasses, silicon wafer, thermoplastic materials, polycarbonate, Poly(methyl methacrylate), polydimethylsiloxane, metals such as titanium or notably quartz. More generally, any material having a high acoustic impedance, that is to say an acoustic impedance at least ten times greater than that of the liquid, may be used. According to one embodiment, the first and the second walls comprise the same or different materials.

The wall facing the wall from which the acoustic waves are generated may include, or notably consist of, a material having an acoustic impedance at least ten times greater than that of the liquid. By using materials having a high acoustic impedance in the walls, it is advantageously possible to improve the acoustic focusing of objects by promoting the formation of a prominent pressure extremum.

The first and second walls of the cavity, for example, be in the form of plates and may have a height in the range from 0.1 mm to 5 mm. One of the wall of the cavity may be opaque. One of the wall of the cavity if transparent. In a variant, both walls are transparent. The use of at least one wall comprising at least one transparent region is required to illuminate the content of the cavity.

The cavity may be in liquid communication with at least one inlet, preferably two or three inlets. The cavity may further be in liquid communication with at least one outlet, preferably two or three outlets.

The cavity inlet(s) and/or outlet(s) may be connected to syringe pumps and/or peristaltic pumps and/or any device that could drive flow. When they are connected to peristaltic pumps, a hydrodynamic dampener may be added between the peristaltic pump and the cavity inlet(s) and/or outlet(s). As such, it may not be necessary to open the cavity in order to collect the formed multilayer aggregates.

The acoustic field is produced by at least one acoustic field generator.

The acoustic field generator may be a piezoelectric material, e.g. ceramic.

According to one embodiment, the acoustic field has for example, an amplitude ranging from 0.1 V to 50 V, preferably from 1 to 10 V.

The acoustic field may have, for example, a frequency less than or equal to 20 megahertz, and notably in the range from 0.5 to 10 megahertz. By using these frequency ranges, it may advantageously be possible to handle living cells without damaging them.

According to one embodiment, the frequency of the acoustic field is in the range from $0.5f_0$ to $1.5f_0$, wherein $f_0$ is a resonance frequency of the cavity. By using this frequency range, close to a resonance frequency, it may advantageously be possible to create a sufficiently large acoustic force to provide satisfactory focusing of the objects. According to one embodiment, the frequency of the acoustic field is about or equal to the resonance frequency of the cavity.

According to one embodiment, the acoustic field is a continuous acoustic field. According to one embodiment, the acoustic field is a pulsed acoustic field. The acoustic wave generator may be supplied with a sinusoidal voltage. In a variant, the acoustic wave generator may be supplied with a triangular or square-wave voltage.

The part of the acoustic field generator in contact with a wall of the cavity may be circular or rectangular. The acoustic wave generator may, for example, be fixed to the first or second wall of the cavity. This fixing may be carried out by any way known to persons skilled in the art, notably by gluing.

According to one embodiment, the part of the acoustic field generator in contact with a wall (the transmitter wall) of the cavity is annular. According to said embodiment, a light beam may pass through the acoustic field generator. According to one embodiment, the objects are submitted to a first light beam emitting at a first wavelength range through the reflective wall and to a second light beam emitting at a second wavelength range through the opening of the annular transducer and the transmitter wall.

A layer of acoustic matching material may be present between the acoustic wave generator and at least one of the first and second walls of the cavity. The acoustic matching may be provided by using any material known to persons skilled in the art as suitable for this purpose, such as glue, acoustic gels, oil . . . .

A plurality of acoustic wave generators may be arranged along the transmitter wall of the cavity and may generate acoustic waves from at least one of the first and second walls, said acoustic wave generators possibly being positioned, on the same side of the cavity.

The use of a plurality of acoustic wave generators is advantageous when the liquid flows at high velocity or when layers of large objects are to be generated. In the first case, the flight time under the generators decreases as the liquid velocity increases. This may require a greater number of transducers to be used in order to achieve focusing. In the second case, in the absence of flow for example, it is possible to use a plurality of acoustic wave generators to form large layers of objects.

When a plurality of acoustic wave generators is used, at least one of them may generate an acoustic wave along the first transverse axis of the cavity, that is to say along the width of the cavity. In the latter case, the width/height ratio may be in the range from 1 to 10, notably from 1 to 3.

By applying an acoustic force field over the height and over the width, it may advantageously be possible to move a set of objects, for example a line of objects, in any area of the cavity, and thus to benefit from a larger number of available locations for the acoustic focusing.

According to one embodiment, at least one light source is configured to emit a light beam in a region of the cavity or in the whole cavity. The at least one light source may be a laser diode, a laser, a diode, a LED or any other light source known to one skilled in the art.

The at least one light source may emit light in the range from 200 nm to 1 000 nm, preferably notably from 360 nm to 800 nm.

According to one embodiment, the power of the light beam emitted by the light source is ranging from 10 μW to 200 mW.

According to one embodiment, the at least one light source may be placed opposite to the wall from which is generated the acoustic field.

According to one embodiment, the at least one light source may be placed on the same wall as the wall from which is generated the acoustic field. In one embodiment, the light source may be emitted through any transparent wall of the cavity.

The at least one image of at least some of the objects that are present within the cavity and that are illuminated by the illumination system may be acquired by an image acquisition system.

In one embodiment, the image acquisition system comprises a microscope, such as an inverted microscope or a reflection microscope. In one embodiment, the image acquisition system further comprises a camera.

In one embodiment, the image acquisition system, has a lens for focusing the radiation from the objects present in the cavity on a sensor, enabling an image of said objects to be produced. The sensor may, for example, be a CCD camera.

The illumination system may be configured to illuminate some or all of a layer of objects formed by acoustic focusing. The illumination system includes a light source which may, for example, include a laser, a diode or a LED.

The at least one image may be processed by a processing device. The processing device may be used to measure the norm and/or direction and/or sense of the velocity vector of at least some of the objects that are present within the cavity and that are illuminated by the illumination system. The assembly according to the invention may, notably, be used to execute a method of object image velocimetry.

The device for processing the at least one image may, for example, include a computer.

The image processing device may, for example, be configured to calculate a correlation coefficient of the distributions of luminous intensity found in at least two images of objects produced by the image acquisition system.

While various embodiments have been described and illustrated, the detailed description is not to be construed as being limited hereto. Various modifications can be made to the embodiments by those skilled in the art without departing from the true spirit and scope of the disclosure as defined by the claims.

REFERENCES

A—Camera
B—Computer
C—Light source
D—Microscope
E—Amplifier
F—Wave generator
1—Device for manipulating objects
2—Cavity
3—Reflective wall
4—Transmitter wall
5—Acoustic wave generator
6—Light source
7—Illumination area
8—Acoustic field
9.1—First inlet
9.2—Second inlet
9.3—Third inlet
10.1—First outlet
10.2—Second Outlet
10.3—Third outlet

EXAMPLES

Acoustic Resonator

Figure 9:
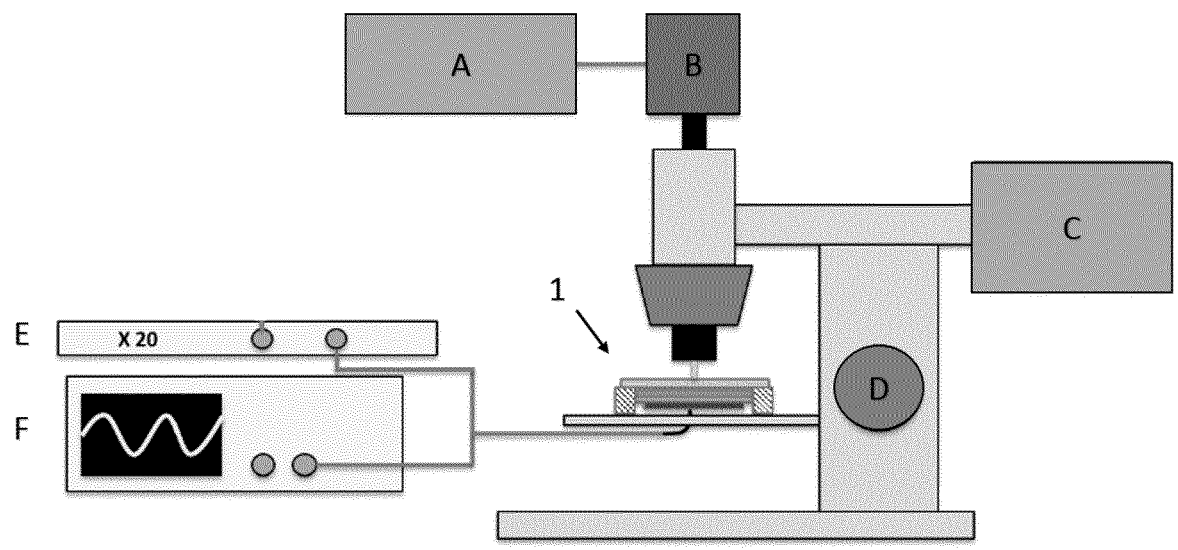
FIG. 9 is a schematic illustration of a device for manipulating objects, an illumination system and an acquisition system according to one embodiment of the invention.

A circular aluminum cavity of diameter D=20 mm and height h=400 µm was manufactured. The cavity is closed by a round quartz cover plate, of height 1.1 mm, acting as the reflective wall while the bottom is made of a silica wafer, of height 0.30 mm, acting as the transmitter wall. A square piezoelectric transducer was positioned in contact to the bottom surface of the cavity. Said piezoelectric transducer, 1 mm height and 10 mm side, was glued directly on the silica wafer using a water-soluble glue. As depicted in FIG. 9, the piezoelectric transducer is powered by a wave generator F (Tabor Electronics 5200) connected to an amplifier E (Tabor Electronics 3222) allowing variation of the applied voltage from a few mV to more than 10 V. The frequency of the sinusoidal signal was tuned to maximize the acoustic radiation force which correspond to the resonance condition, i.e. a wavelength of twice the height of the cylindrical cavity, here 1.85 MHz.

Illuminating System and Acquisition System

The illumination system comprises a light source C which allows both white light for imaging as well as a good control of the wavelength of the light beam. The acquisition system comprises an microscope D, and recording were made using a high speed camera B connected to a computer A.

Breakup of Aggregates of Fluorescent Objects

Figure 10:
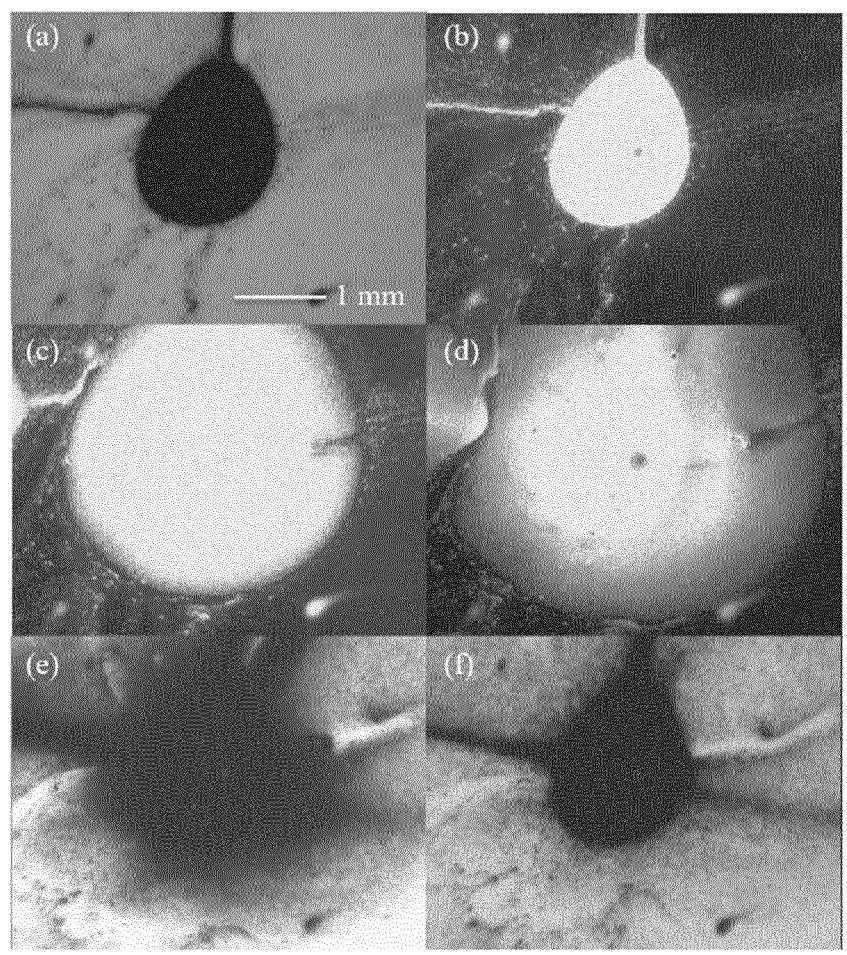
FIG. 10 illustrates an aggregate of 1.6 μm objects:
(a) submitted to green illumination ($\lambda_{light}$=545 nm);
(b) fluorescing in red;
(c)-(d) under the photoacoustic interaction, the aggregate explodes (c)-(d)

Fluorescent polystyrene particles of diameter $d_p$=1.62 µm which can be excited with green light and fluoresce in red light ($\lambda_{abs}$=532 nm and $\lambda_{em}$=600 nm) were used. The particles were dispersed in a liquid. Experiments were carried out at a frequency of 1.849 MHz, a transducer supply voltage of 7 V and an illumination power of 20.4 µW. As illustrated in FIG. 10, large aggregates of particles are created in acoustic levitation. Once a green light beam illuminates the aggregates in acoustic levitation, the aggregate starts to eject particles. The particles escape the aggregate while remaining in levitation. According to the Applicant, this is due to the fact that the primary radiation force is not affected but the transversal force is balanced. Once the light beam is turned off, the aggregation process starts again. It appears that the ejection of particles occurs for various voltages and various illumination powers and, as shown in FIG. 11 and FIG. 12, that the ejection speed increases with increasing illumination and increasing amplitude.

Experiments have been carried out and the effect according to the invention has been validated on particles of different sizes (from 1 to 15 µm), different materials (latex, polystyrene, silicon), different colors (the effect is observed with non-fluorescent colored particles) and different fluorescences.

FIGS. 15a, 15b and 15c are time lapse fluorescent microscope images of an explosion of 1.0 µm fluorescent polystyrene particles (Micromod). The excitation light is blue (GFP filter) and the power light is at its maximum (100% on the control panel and maximal opening of the aperture diaphragm i.e. about 160 mW.mm-2, from light power meter measurement done by Dumy). The frequency of the acoustic wave is 1.91 MHz. The amplitude of the electrical signal coming from the generator is 300 mV.

Influence of the Size of the Objects

The operating conditions detailed in the part "Breakup of aggregates of fluorescent objects" above were repeated for different diameters of fluorescent or absorbing objects. Fluorescent objects of diameters ranging from 0.883 µm to 5 µm and absorbing objects of diameters ranging from 10 µm to 15 µm were used. It appeared that the diameter of the objects has no effect of the expulsion phenomenon. But according to other experimental conditions and the nature of particles or cells, the size may have an effect on the expulsion phenomenon.

Breakup of Aggregates of Red Blood Cells

Experiment were also carried out with red blood cells. Red blood cells are non-fluorescing particles absorbing in the range of wavelength from 400 to 500 nm. The experiments were conducted at a frequency of 1.850 MHz, a transducer supply voltage of 6 V and an illumination power of 20.4 mW. As illustrated in FIG. 13, large aggregates of red blood cells are created in acoustic levitation. Once a blue light beam illuminates the aggregates in acoustic levitation, the aggregate starts to eject particles. The particles escape the aggregate while remaining in levitation. Once the light beam is turned off, the aggregation process starts again.

Separation of Mixed Solution of Two Colloidal Particles

A mixed solution of fluorescent colloidal particles: polystyrene particles of diameter $d_{p1}$=1.62 µm and $d_{p2}$=0.883 µm, with absorption wavelengths $\lambda_1$=545 nm and $\lambda_2$=488 nm and with equal volume fraction (0.025%) was used. The mixture was focused into an aggregate using a supply voltage of 10.5 V and a frequency of 1.903 MHz. The aggregate was then illuminated with a blue light $\lambda_{light}$=488 nm at a power of 20 µW for 10 seconds. As illustrated in FIG. 14 a), b) and c), before illumination, the aggregate created by the acoustic force is homogeneous (b shows the green fluorescent particles and c the red fluorescent particles). The pictures at the bottom show the aggregate after applying illumination to the particles. The green fluorescent particles e) have been extracted from the red ones f) creating two aggregates, one containing the red particles, the other one containing the green particles.

Breakup of Aggregates of Micro-Algae

Explosions of levitating aggregates of micro-algae (Phacodactylum) were made in a 2 MHz resonator. Other type of algae, called Porphyrydium, did not form aggregates maybe because they had a density very close to the one of water (they sedimentate very slowly).

The typical size of micro-algae Phacodactylum is about 2 µm. FIG. 16 shows a brightfield image of a levitating aggregate of algae Phacodactylum in a 2 MHz resonator. Once the aggregate has been formed (first picture on the left side), it is illuminated with the blue light by positioning the filter cube on GFP (Green Fluorescence Protein) during 5 seconds. When the filter cube is turned back to the brightfield position, the algae moved (central picture). Then, under the action of the acoustic forces, the aggregate reforms and recovers its original shape under the action of the acoustic forces (right side picture). Note that the green light (DsRED filter) has no effect on the aggregate. This example shows that the blue light can selectively explode a micro-algae aggregate.

Other tests with micro-algae are planned. The Porphyrydium micro-algae was tested and no effect was observed at all, not even the acoustic levitation. The Porphyrydium density is close to the one of water, so that the acoustic force is close to zero. This is confirmed by the fact that no sedimentation is observed for this algae.

Breakup of Aggregates of Cells Labeled with a Fluorescent Marker

Manipulated stem cells have not revealed any specific light absorption peaks after passage through a spectrophotometer. No effect was observed when these stem cells were illuminated with different wavelengths and maintained in acoustic levitation.

An effect was observed when worked with fluorescently labeled cells (immunofluorescence). In this case, the cell aggregates could be moved under the effect of selective illumination at the wavelength of the fluorescent marker. This confirms that the opto-acoustofluidic effect can be generalized to all types of cells labeled on the surface with a fluorescent marker. It is possible to sort based on specific properties of the cells since the fluorescent markers (fluorescent labeled antibodies) are fixed on the membrane of the cells according to the antigens present. This can be useful for specific cell sorting, cell therapy for example. It can also be very effective in identifying and separating cells with a specific marker, such as cancer stem cells that can be detected by a fluorescent marker.

Breakup of Aggregates of Nano-Rods

Nano-rods of different shapes were created from different materials, metals or polymers containing a fluorophore or being naturally fluorescent. Nano-rods are sticks with diameter less than one micron. Under the effect of the acoustic field, nano-rods form an aggregate, see FIG. 17. Unlike particle aggregates, nano-rods are mobile within the aggregate. When it is illuminated at the right wavelength, the aggregate explodes. It thus appears possible to couple acoustic force and selective illumination to control the movement of one or more nano-rods.

Isolation of a Rare Cell in the Middle of a Large Number of Light-Sensitive Particles When particles that absorb light at a certain wavelength are illuminated in the acoustic focus plane, they are expelled from the illuminated area but remain in acoustic levitation. This principle may be used to isolate rare cells, such as Circulating Tumor Cells (CTC).

FIG. 18 illustrates an example of isolation of large light-insensitive particles surrounded by a large number of particles that absorb light. The first step is to form an aggregate containing both types of particles (t=0). Then an illuminate was made at the absorption wavelength of the small particles. These later are ejected out of the illuminated area. After a few minutes, only the large particles remain in the aggregation zone. These conditions are similar to those observed for rare cells (large and not sensitive to light) surrounded by red blood cells (smaller, very numerous and sensitive to light).

Indeed, it is demonstrated that red blood cells (RBCs) can be expelled from the illuminated area if the right wavelength (488 nm) is used. The main difficulty in finding rare cells in the blood is precisely that they are rare and mixed with a very large number of RBCs that mask all other cells. By illuminating a blood suspension at 488 nm, the RBCs will be expelled and it will then be possible to observe the plasma and all other cells that do not absorb this wavelength. CTCs are relatively large cells (about 30 □m) and should be easy to observe and recover because they will quickly migrate to the sound pressure node.

In order to validate this principle of rapid detection of rare cells, experiments were carried out in similarities with a mixture of many small fluorescent particles (approximately 3 µm) with some large non-fluorescent particles (30 µm). The result is that expected: the small particles are expelled from the illuminated area while the large particles remain in levitation aggregate in the acoustic focus zone, insensitive to illumination. After a few minutes, only the large particles of acoustic levitation remain in the illuminated area (FIG. 18).

The invention claimed is:

1. A method for manipulating objects in a cavity comprising a liquid, said method comprising:
   a) providing objects in at least one region of the cavity;
   b) forming an aggregate of the objects within a levitation plane by submitting them to an acoustic field; and
   the objects are light absorbing objects in a given wavelength range, and said method further comprising the step of:
   c) disrupting the aggregate within the levitation plane by submitting said aggregate to a light beam emitting at the said given wavelength range, the objects migrating along the levitation plane and being gradually expulsed from the aggregate itself.

2. The method according to claim 1, wherein a power of the light beam is ranging from 10µW to 200 mW.

3. The method according to claim 1, wherein an amplitude of the acoustic field is ranging from 0.1 V to 50 V.

4. The method according to claim 1, wherein a volume fraction of the objects within the liquid is ranging from 0.025% to 65%.

5. The method according to claim 1, wherein the acoustic field (8) is a pulsed acoustic field.

6. The method according to claim 1, wherein a frequency of the acoustic field is in the range from $0.5f_o$ to $1.5f_o$, wherein $f_o$ is a resonance frequency of the cavity.

7. The method according to claim 1, wherein the objects are fluorescents.

8. A method for separating objects in a cavity comprising a liquid, said method comprising:
   a) providing in at least one region of the cavity objects comprising a first plurality of objects capable of absorbing light in a first wavelength range and a second plurality of objects not capable of absorbing light in the first wavelength range;
   b) forming an aggregate within a levitation plane of the first plurality of objects and the second plurality of objects by submitting them to an acoustic field; and
   c) expulsing within the levitation plane the first plurality of objects from the aggregate by submitting the aggregate comprising first plurality of objects and second plurality of objects to a light beam emitting at the said first wavelength range, the first plurality of objects migrating along the levitation plane and being gradually expulsed from the aggregate itself.

9. The method according to claim 8, further comprising the steps of:
   flowing the liquid within the cavity; and
   recovering the expulsed objects in a first outlet.

10. The method according to claim 8, wherein the second plurality of objects absorbs light in a second wavelength range not overlapping with the first wavelength range.

11. The method according to claim 10, further comprising the step of submitting the aggregate to a light beam emitting at the second wavelength range.

12. The method according to claim 8, wherein the first plurality of objects has a same acoustic contrast factor than the second plurality of objects.

13. A method for acquiring at least one image of objects in a cavity comprising a liquid, said method comprising:
   a) manipulating or separating the objects by using the method as claimed according to claim 1;
   b) illuminating the at least one region of the cavity; and
   c) acquiring at least one image of said illuminated objects through a transparent wall of the cavity.

14. A device for separating objects in a liquid, said device configured for performing the method of claim 1 and comprising:
   at least one cavity extending along a longitudinal axis, having a cross-section that present a width (w) measured along a first transverse axis and a height (h) measured along a second transverse axis perpendicular to the first transverse axis; the cavity having first and second walls along the second transverse axis, at least a first inlet in liquid communication with the cavity and at least first, second and third outlets in liquid communication with the cavity, wherein the first outlet is arranged on the first transverse axis between the second and third outlets;
   at least one acoustic wave generator which generates acoustic field in a first region of the cavity from one of the walls; and
   at least one light source is arranged to emit simultaneously to the acoustic field a light beam in the first region of the cavity, the at least one light source being placed opposite to or on the same wall from which is generated the acoustic field, said light source being configured to emit a light beam at a wavelength corresponding to the absorbing wavelength range of the objects.

15. The device according to claim 14, further comprising second and third inlets, wherein the first inlet is arranged on the first transverse axis between the second and third inlets.

* * * * *